United States Patent [19]

Balasubramanian et al.

[11] Patent Number: 5,248,673
[45] Date of Patent: Sep. 28, 1993

[54] BISAMIDINE DERIVATIVES AS THROMBIN INHIBITORS

[75] Inventors: Neelakantan Balasubramanian, Bristol; William T. Han, Cheshire, both of Conn.

[73] Assignee: Bristol-Myers Squibb Co., New York, N.Y.

[21] Appl. No.: 995,481

[22] Filed: Dec. 23, 1992

[51] Int. Cl.⁵ .................. A61K 31/535; A61K 31/55; C07D 211/16; C07D 295/192

[52] U.S. Cl. .................. 514/212; 514/237.5; 514/319; 540/607; 544/159; 546/206; 546/226

[58] Field of Search .................. 540/607; 544/159; 546/206, 226; 54/212, 237.5, 319

[56] References Cited

U.S. PATENT DOCUMENTS 4,041,156  8/1977  Okamoto et al. .
4,374,248  2/1983  Crenshaw et al. .
4,440,933  4/1984  Montzka .
4,537,896  8/1985  Cleason et al. .

OTHER PUBLICATIONS

John E. Starrett, Jr., et al., *J. Med. Chem.*, 32: 2204 (1989).
Bajusz, et al., *Int. J. Pept. Protein Res.*, 12: 217-221 (1978).

*Primary Examiner*—Robert W. Ramsuer
*Attorney, Agent, or Firm*—Michelle A. Kaye

[57] ABSTRACT

The present invention provides new thrombin inhibiting bisamidines derivatives, their pharmaceutically acceptable salts and hydrates, methods for their preparation, pharmaceutical composition, a process for their preparation, and use of the compounds in treatment of thrombosis, ischemia and stroke.

15 Claims, No Drawings

BISAMIDINE DERIVATIVES AS THROMBIN INHIBITORS

BACKGROUND OF THE INVENTION

1. Field of the Invention

This invention relates to novel thrombin inhibiting bisamidine derivatives, their salts and hydrates and to a process for the preparation thereof. The compounds of this invention are useful under conditions of thrombosis, ischemia or stroke.

2. Description of the Art

Thrombosis can be regarded as a pathological condition where improper regulation of the hemostatic mechanism results in the formation of intravascular thrombi which may lead to tissue damage or death due to inadequate blood flow. This condition is a major cause of mortality and morbidity in humans. Thrombin plays many crucial roles in hemostasis and thrombosis The serine protease activity of thrombin is required for the cleavage of fibrinogen to fibrin polymer and also for platelet activation. In the presence of the coagulation factor XIIIa, this polymer undergoes crosslinking and forms the insoluble fibrin clot. The development of agents to inhibit thrombin generation and activity in prethrombotic situations could be useful for control of blood coagulation and could greatly aid in lowering the incidence of thrombus-induced myocardial and cerebral ischemia.

Substituted bisamidines of the Formula I are known intermediates in the preparation of certain anti-ulcer agents of the Formula II. U.S. Pat. Nos. 4,374,248 and 4,440,933 disclosed and claimed a series of I and II as anti-ulcer agents.

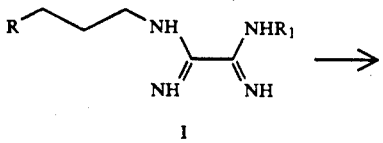

I

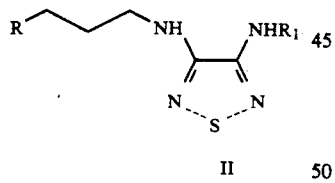

II

John E. Starrett, Jr., et al., in a recently published article (J. Med. Chem., 32: 2204 (1989)) disclosed selected bisamidine containing imidazo[1.2-a]pyridines (Formula III) as a key intermediate in the preparation of antiulcer agents.

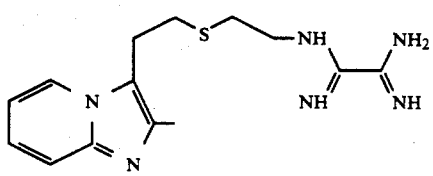

III

Okamoto, et al., U.S. Pat. No. 4,041,156 and Cleason, et al., U.S. Pat. No. 4,537,896 disclosed a number of arylsulfonyl arginine amides and p-guanidino phenyl alanine amides of the general Formula IV and V useful as thrombin inhibitors.

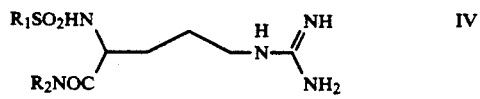

IV

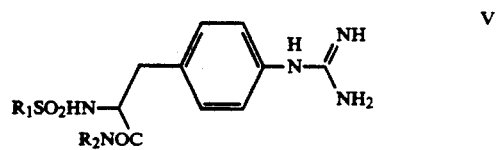

V

Bajusz, et. al., in Int. J. Pept. Protein Res., 2:217–221 (1978) discloses peptide aldehydes of the Formula VI which have thrombin inhibitory properties.

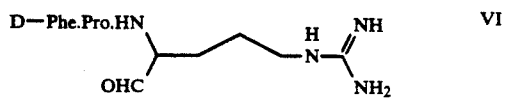

VI

There is nothing in any of the foregoing references, to suggest the novel thrombin inhibitors bisamidine derivatives of the present invention.

SUMMARY OF THE INVENTION

The present invention provides novel bisamidine derivatives having the Formula VII (below) their pharmaceutically acceptable salts and hydrates thereof.

Also provided is a process for the preparation of the compounds of Formula VII.

Also provided is a method of treating thrombosis, ischemia or stroke in a mammalian host in need thereof which comprises administering to said host an effective amount of at least one compound of Formula VII.

Firther provided is a pharmaceutical composition which comprises the compounds of Formula VII and one or more pharmaceutically acceptable carrier or diluent.

DETAILED DESCRIPTION OF THE INVENTION

The present invention provides novel bisamidine derivatives having the formula VII

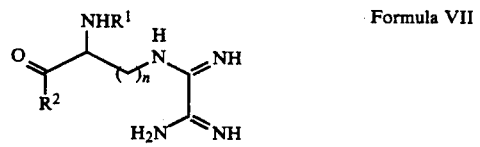

Formula VII wherein
$R^1$ is dimethylaminoaphthalenesulfonyl, p-toluene sulfonyl or 2-naphthylene sulfonylglycine;
$R^2$ is piperidine, substituted piperidine, wherein the substituents are $C_1-C_5$ alkyl, carboxylic acid, N-substituted amino acid esters wherein the subtituents are $C_1-C_5$ alkyl, morpholine, and homopiperidine; and
n is 1-5;
their salts and hydrates thereof.

Of the compounds of this invention, it will be understood that the following compounds of Formula VII whereinin $R^1$ is 5-dimethylaminonaphthalenesulfonyl and $R^2$ is unsubstituted or substituted piperidine is preferred. The compound 1-[5-[(2-Amino-1,2-diiminoethyl)amino]-2-[[[5-(dimethylamino]-1-naphthalenyl]sulfonyl]amino]-1-oxopentyl]-4-ethylpiperidine is the most preferred.

As used herein and in the claims, unless otherwise indicated, the term "$C_1$–$C_5$ alkyl" is meant to include methyl, ethyl, propyl, butyl and pentyl.

The general synthetic sequence employed in the preparation of a series of bis-amidines is outlined in Scheme I. The starting amino acids are readily obtained from commercial sources or following literature methods (*Collect. Czech. Chem. Comm.*, 25: 2022 (1960)). Treatment of amino acids 1 with appropriate acid chloride under standard conditions using 2N alkaline hydroxide such as sodium hydroxide in a polar organic solvent like dioxane, dimethylforamide or acetonitrile, preferably in temperature provided the amino acid derivatives 2 after standard aqueous workup. Coupling of the acids 2 with the appropriate amine such as substituted or unsubstituted piperidine under the normal peptide coupling conditions using reagents such as hydroxybenztriazole (HOBT), hydroxy succinimide, 1,3-dicyclohexylcarbodiimide (DCC), carbonyldiimidazole (CDI), isobutylchloroformate/NEt$_3$ and most preferably diphenylphosphonylazidate (DPPA)/NEt$_3$ provided the amide derivatives 3 after usual workup. Removal of the protecting group such as the carbobenzyloxy (CBz) under hydrogenolysis condition, preferably with H$_2$/Pd/C at 1 atmosphere in the presence of an acid such as HCl, H$_2$SO$_4$ gave the desired intermediate amines 4 as their salts. Reaction of the amines 4 with methoxythiadiazole S-oxide 5 (U.S. Pat. No. 4,374,248) in refluxing methanol for 1–5 hours gave the thiadiazole S-oxide intermediate 6. Hydrolysis of 6 under acidic conditions such as 6N HCl furnished the bisamidines 7 as their salts.

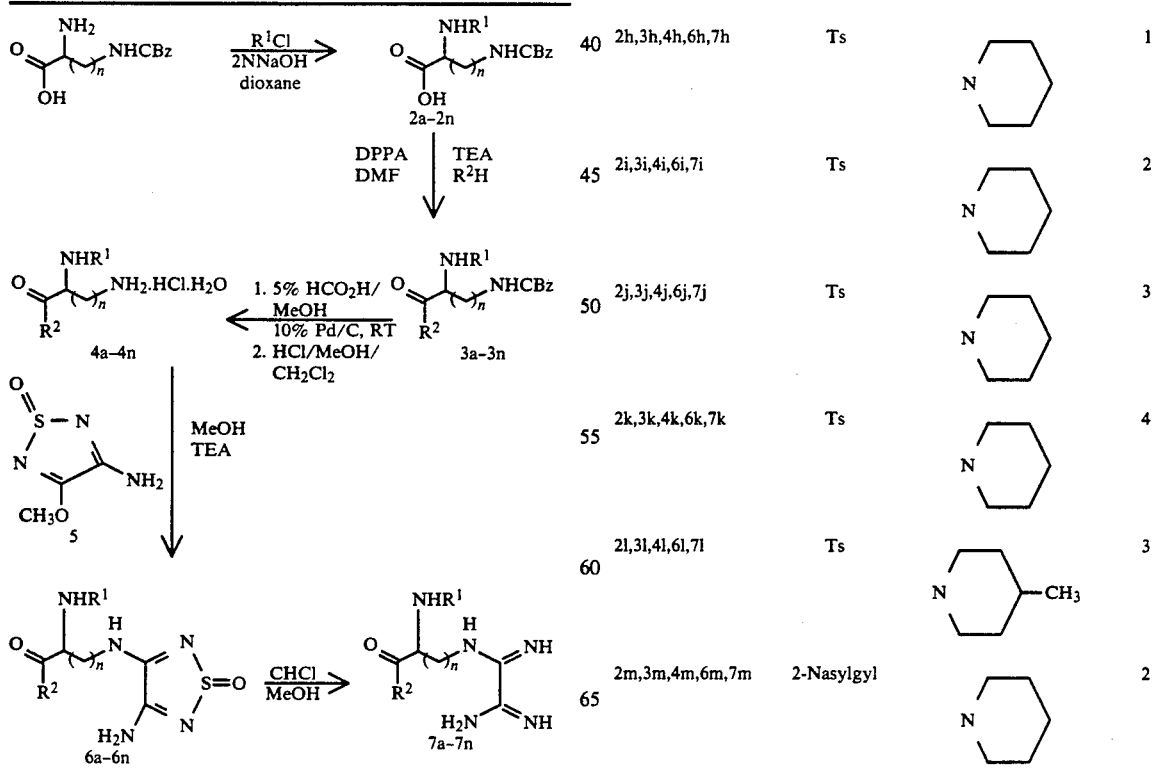

Scheme I -continued 2n,3n,4n,6n,7n     2-Nasylgyl     3

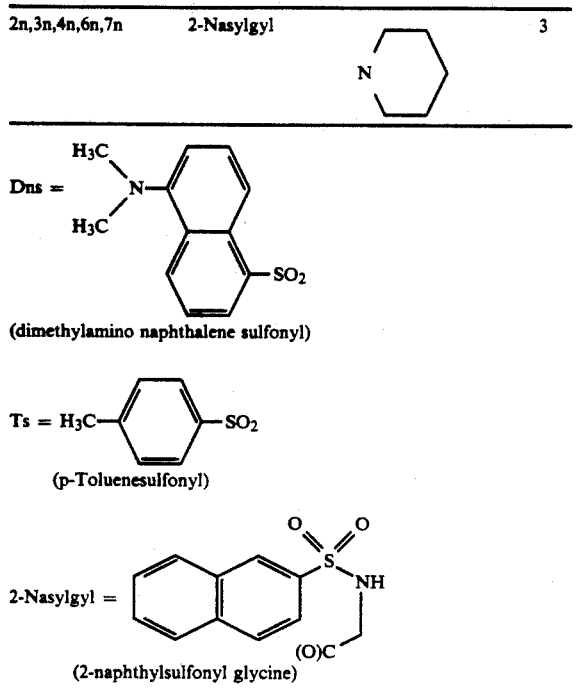

Dns = (dimethylamino naphthalene sulfonyl)

Ts = (p-Toluenesulfonyl)

2-Nasylgyl = (2-naphthylsulfonyl glycine)

Biological Evaluation

Enzyme Assays for the Inhibition of Thrombin
The following reagents were used in these assays:
Thrombin assay buffer: 145 mM NaCl, 5 mM KCl, 30 mM MN-2-hydroxyethyl piperazine-N'-2-ethanesulfonic acid, pH 7.4, 1 mg/ml polyethylene glycol (PEG-8000). 3 mM D-Phe-Pip-Arg-p-nitroanilide (s-2238) in $H_2O$. 3 U/ml purified human α-thrombin dissolved in thrombin assay buffer.

Inhibitors to be tested were dissolved in $H_2O$, methanol, or DMSO just prior to use.

Assay Procedure

To each well in a 96-well microtiter plate, 270 μl of assay buffer was added. Human α-thrombin (10 μl of 3 U/ml) was added, then 10 μl of inhibitor were added and mixed. The samples were incubated at room temperature for a defined period of time (3 minutes for initial $IC_{50}$ determinations). The enzymatic reaction was started with 10 μl of 3 mM s-2238 substrate and continued at room temperature. The change in optical density was measured at 405 nm. A kinetic microplate reader (Molecular Devices Corporation $v_{max}$) was used to measure the change in optical density over time.

Results are reported in Table I as $K_i$ values. Table I lists the $K_i$ values for different compounds, $K_i$ value is determined graphically from Dixon plots (plots of reciprocal enzyme velocity i/v vs. linear function of inhibitor concentration at various enzyme substrate concentrations). This methodology is well known in the art.

Procedure for Determining the Concentration Required for Doubling Thrombin Clotting Time—Clotting Time Assays The following reagents were used in these assays:
Owren's Veronal Buffer: 125 mM NaCl, 28.4 mM sodium barbital, pH 7.35.

Human citrated plasma obtained from human volunteers or citrated plasma obtained from dosed animals (prepared as described below). 25 NIH Units/ml human α-thrombin in thrombin buffer for use with rat plasma. 10 NIH Units/ml human α-thrombin in thrombin buffer for use with human plasma.

Preparation of the Citrated Plasma

Human Plasma: Blood from human volunteers was drawn into vacutainer tubes containing one tenth final volume of 0.129M (3.8%) buffered citrate (16 mg Sodium Citrate $2H_2O$ and 2.1 mg citric acid per milliliter of $H_2O$). The blood was centrifugated at (using a Sorvall RT 6000B centrifugate). The plasma was removed, pooled, and aliquoted into small tubes which were stored frozen for later use.

Dosing: Test compound was prepared just prior to dosing. Routinely the drugs are dissolved in water. Occasionally other vehicles are used, such as PEQ-200 stock solutions are vortex mixed and animals are dosed p.o. using a 3 ml syringe with an 18–19 gauge oral gavage needle or i.p. injection.

Blood Drawing for Rats: After the appropriate time period, the animals were ether-anesthetized, and blood was drawn by cardiac puncture using 333 μl of 3.8% sodium citrate per 3 ml blood. After all of the samples were obtained, the tubes were centrifuged at 1,500 rpm for 15 minutes as described for the human blood samples.

Clotting Time Measurement

Clotting times were determined by pipetting 0.1 ml of Owren's buffer (pre-warmed to 37° C.) and 0.1 ml of human or rat plasma into yellow sample cuvettes. For studies with human plasma 10 U/ml human thrombin (10 ml) was placed in the reservoir assembly station of the MLA 700. (Medical Laboratory Automation, Electra 700 Reservoir Assembly). For rat studies, the human thrombin concentration was 25 U/ml. The cuvettes were vortexed and then placed on the MLA 700 sample wheel. The coagulation timer (MLA 700) automatically dispenses 0.1 ml human thrombin into the sample in each cuvette. Detection of the fibrin clot was determined optically by the MLA 700.

Studies were performed to determine the concentration of drug which caused a doubling of the clotting time (DTT) in human plasma. From standard curves of thrombin activity added to the sample versus the clotting time, the concentration of drug which caused a doubling of the thrombin clotting time corresponded to inhibition of approximately 12 of the added thrombin clotting activity. Table II shows representative examples of compounds claimed herein. Table II shows that the compounds of the present invention are effective in prolonging thrombin clotting time and therefore are efficient antithrombin agents.

The biological results obtained show that the compounds of the present invention exhibit antithrombin activity and are thus useful in the treatment of thrombosis, ischemia and stroke.

TABLE I
Biological Evaluation of Bisamidines.

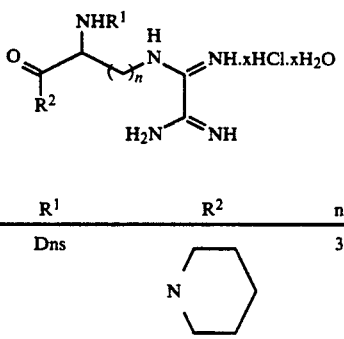

| Compound | R¹ | R² | n | $K_i$ (μM) |
|---|---|---|---|---|
| 7a | Dns | 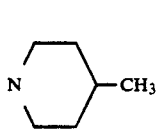 | 3 | 3.2 |
| 7b | Dns | 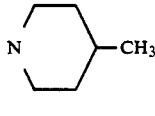 | 2 | 4.0 |
| 7c | Dns | 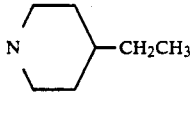 | 3 | 0.33 |
| 7d | Dns | 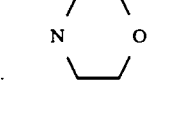 | 3 | 0.3 |
| 7e | Dns | 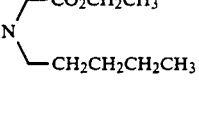 | 3 | 2 |
| 7f | Dns | 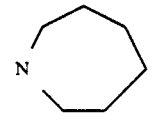 | 3 | 3 |
| 7g | Dns | 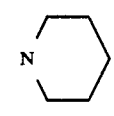 | 3 | 0.4 |
| 7h | Ts | 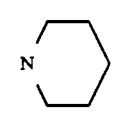 | 1 | insol. |
| 7i | Ts | 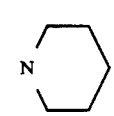 | 2 | 80 |
| 7j | Ts | 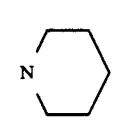 | 3 | 16 |
| 7k | Ts | 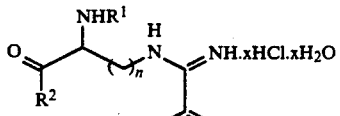 | 4 | 55 |
| 7l | Ts | 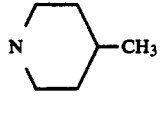 | 3 | 18 |
| 7m | 2-Nasylgyl | 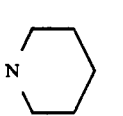 | 2 | 36 |
| 7n | 2-Nasylgyl | 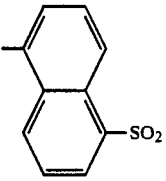 | 3 | >50 |

Dns = 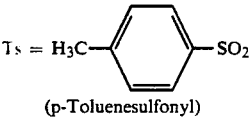
(dimethylamino naphthalene sulfonyl)

Ts = H₃C—⟨ ⟩—SO₂
(p-Toluenesulfonyl)

2-Nasylgyl = 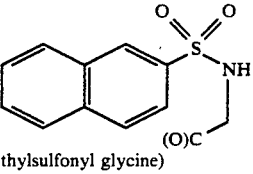
(2-naphthylsulfonyl glycine)

TABLE II
Biological Evaluation of Bisamidines.

| Compound | DTT (μM) |
|---|---|
| 7c | 1.0 |
| 7d | 0.92 |
| 7e | 4.0 |
| 7f | 15 |
| 7g | 1.8 |
| 7h | >300 |
| 7k | 150 |

For therapeutic use, the pharmacologically active compounds of Formula VII will normally be administered as a pharmaceutical composition comprising as the (or an) essential active ingredient at least one such compound in the basic form or in the form of a nontoxic pharmaceutically acceptable salt, in association with one or more pharmaceutically acceptable carriers.

Administration of the active compounds, salts and hydrates described herein can be via any of the accepted modes of administration for systemically active therapeutic medications. These methods include oral, nasal, parenteral and otherwise systemic forms.

Depending on the intended mode of administration, the compositions used may be in the form of solid, semisolid or liquid dosage forms, such as, for example, tablets, suppositories, pills, capsules, powders, liquids, aerosols, suspensions, or the like, preferably in unit dosage forms suitable for single administration of precise dosages. The compositions will include a conventional pharmaceutical carrier or excipient and an active compound of the Formula (I) or the pharmaceutically acceptable salts or hydrates thereof and, in addition, may include other medicinal agents, pharmaceutical agents, carriers, adjuvants, etc.

For solid compositions, conventional non-toxic solid carriers include, for example pharmaceutical grades of mannitol, lactose, starch, magnesium sterate, sodium saccharin, talcum, cellulose, glucose, sucrose, magnesium carbonate, and the like may be used. The active compound as defined above may be formulated as suppositories using, for example polyalkylene glycols, for example propylene glycol, as the carrier. Liquid pharmaceutically administrable compositions can, for example, be prepared by dissolving, dispersing, etc. an active compound as defined above and optional pharmaceutical adjuvants in a carrier, such as, for example water, saline, aqueous dextrose, glycerol, ethanol, and the like, to thereby form a solution or suspension. If desired, the pharmaceutical composition to be administered may also contain minor amounts of non toxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example see *Remington's Pharmaceutical Sciences*, Mack Publishing Company, Easton Penna., 15th Edition, 1975. The composition or formulation to be administered will, in any event, contain a quantity of the active compound(s) in an amount effective to alleviate the symptoms of the subject being treated.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like.

Physicians will determine the dosage of the present therapeutic agents which will be most suitable. The dosage of the compounds of this invention will depend not only on such factors as the mode of administration, and the particular compound chosen, but also on the particular patient under treatment. Generally, dosage will range from about 0.1 mg/kg to about 500 mg/kg.

All publications cited in this specification are indicative of the level of skill of those in the art to which this application pertains. Each publication is individually incorporated herein by reference in the location where it is cited.

The present invention is illustrated by the following examples which are not intended to be construed as limiting the scope of the invention.

In the following examples, all temperatures are given in degrees Centigrade. Melting points were recorded on a Thomas-Hoover capillary melting point apparatus and boiling points were measured at specific pressures (mm Hg) and both temperatures are uncorrected. Proton magnetic resonance ($^1$H NMR) spectra were recorded on a Bruker AM 300, Bruker WM 360 or Varian T-60 CW spectrometer. All spectra were determined in $CDCl_3$, DMSO-$d_6$ or $D_2O$ unless otherwise indicated and chemical shifts are reported in $\delta$ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; and dd, doublet of doublet. Carbon-13 nuclear magnetic resonance ($^{13}$C NMR) spectra were recorded on a Bruker AM 300 or Bruker WM 360 spectrometer and were broad band proton decoupled. All spectra were determined in $CDCl_3$ DMSO-$d_6$ or $D_2O$ unless otherwise indicated with internal deuterium lock and chemical shifts are reported in $\delta$ units downfield from tetramethylsilane. Infrared (IR) spectra were determined on a Nicolet MX-1 FT spectrometer from 4000 $cm^{-1}$, calibrated to 1601 $cm^{-1}$ absorption of a polystyrene film and are reported in reciprocal centimeters ($cm^{-1}$). Relative intensities are indicated as follows; s(strong), m(medium) and w(weak).

Gas chromatography-mass spectra (GC-MS) were determined on a Finnigan 4500 Gas chromatography-quadruple mass spectrometer at ionization potential of 70 eV. Mass spectra were also recorded on a Kratos MS-50 instrument utilizing the fast atom bombardment (FAB) technique. The mass data are expressed in the format: parent ion (M+) or protonated ion (M+H)+.

Analytical thin-layer chromatography (TLC) was carried out on precoated silica gel plates (60F-Z54) and visualized using UV light, iodine vapors and/or staining with one of the following reagents: (a) methanolic phosphomolybdic acid (2%) and heating; (b) reagent (a) followed by 2% cobalt sulphate in 5M H and heating. Column chromatography, also referred to as flash column chromatography, was performed in a glass column using finely divided silica gel (32–63 $\mu$m on silica gel-H) and pressures somewhat above atmospheric pressure with the indicated solvents. All evaporations of solvents were performed under reduced pressure. As used herein, the term hexanes is a mixture of isomeric $C_6$ hydrocarbons as specified by the American Chemical Society, and the term "inert" atmosphere is an argon or nitrogen atmosphere unless otherwise indicated.

EXAMPLE 1

Preparation of 2-[[[5-(dimethylamino)-1-naphthalenyl]sulfonyl]amino]-5-[[(phenylmethoxy)carbonyl]amino]pentanoic acid (2d)

$N^\delta$-Carbobenzyloxy-L-ornithine (39.6 g, 0.149 mol) was dissolved in a solution of 2N NaOH (90 mL) and tetrahydrofuran (200 mL) under nitrogen. After about 15 minutes at ambient temperature, the mixture was cooled to about 0° C. and subsequently treated with additional 2N NaOH (85 mL) and dansyl chloride (45.0 g, 0.167 mol) in 5 g portions over 15 minutes. The mixture was stirred at about 0° C. for about 1 hour and at room temperature for about 2 hours before it was neutralized to pH 7 with 1N HCl. The precipitate was suction-filtered and the filtrate was diluted with ethyl acetate. The organic phase was then separated, washed with brine, dried over $Na_2SO_4$ and concentrated to give a combined yield of 103.17 g (70.4%, two runs) of 2d as a yellow foam which was used directly.

EXAMPLE 2

Preparation of phenylmethyl [4-[[[5-(dimethylamino)-1-naphthalenyl]sulfonyl]amino]-5-[4-ethyl-1-piperidinyl]-5-oxopentyl]carbamate (3d)

To a cold (0° C.), nitrogen-blanketed mixture of 2d (48.90 g, 0.098 mol), triethylamine (25.0 mL, 0.18 mol) and 4-ethylpiperidine (20.0 g, 0.18 mol) in anhydrous dimethylformamide (160 mL) was added dropwise diphenylphosphoryl azide (21.1 mL, 0.098 mol). The mixture was stirred at about 0° C. for about 1 hour and at ambient temperature for about 2 hours before it was partitioned between ether (150 mL) and water (80 mL). The ethereal layer was separated and the aqueous layer was extracted four additional times with ether (80 mL). The combined ethereal extracts were then washed with saturated sodium bicarbonate solution and brine prior to drying ($Na_2SO_4$) and solvent concentration. Two identical reactions were performed in tandem. Purification of the combined residues by HPLC on silica gel (elution with 50% ethyl acetate in hexane) furnished 53.09 g (45%) of 3d as a yellow foam, m.p. 56°-62° C. (dec.); $^1H$ NMR (CDCl$_3$) δ 8.47 (d, 1H), 8.30 (t, 1H), 8.16 (d, 1H), 7.58 (m, 1H), 7.56-7.36 (m, 6H), 7.15 (d, 1H), 6.17-5.96 (dd, 1H), 5.10 (s, 2H), 4.75-4.62 (bm, 1H), 4.10-3.91 (bm, 2H), 3.42-3.30 (bm, 1H), 3.16-2.92 (bm, 2H), 2.85-2.83 (d, 6H), 2.68-2.41 (dt, 1H), 2.24-1.97 (m, 1H), 1.57-0.76 (m, 3H), 0.16-0.08 (m, 1H); $^{13}C$ NMR (CDCl$_3$) ppm 168.50, 156.40, 151.62, 136.50, 135.00, 134.70, 130.56, 130.44, 129.80, 129.35, 129.18, 128.50, 128.41, 128.07, 128.00, 123.01, 122.93, 119.33, 115.58, 115.47, 66.60, 52.29, 52.19, 45.70, 45.43, 45.37, 45.13, 42.02, 42.21, 40.35, 40.18, 37.48, 37.34, 32.17, 31.92, 31.06, 30.79, 30.65, 29.67, 28.77, 28.58, 25.12, 11.08; IR (KBR, cm$^{-1}$) 33,50 2975, 2975, 2950, 1725, 1650, 1550, 1475, 1350, 1275, 1180, 1160; MS m/z (MH$^+$) 595.

Anal. Calcd for $C_{32}H_{42}N_4O_5S$: C, 64.62; H, 7.11; N, 9.41.

Found: C, 64.07; H, 7.29; N, 9.23.

EXAMPLE 3

Preparation of 1-[5-amino-2-[[[5-(dimethylamino)-1-naphthalenyl]sulfonyl]amino]-1-oxopentyl-4-ethylpiperidine dihydrochloride 14d)

Carbamate 3d (24.00 g, 0.040 mol) was added in one portion to a well-stirred, nitrogen-blanketed suspension of 10% palladium on carbon in a 5% formic acid/methanol mixture (350 mL). The reaction mixture was stirred at room temperature for about 3 hours before it was suction-filtered through Celite. The solvent was removed in vacuo and the residue was taken up in dichloromethane, washed with 1N NaOH and brine prior to drying ($Na_2SO_4$) and solvent evaporation. Two identical reactions were performed in tandem. The free amine was obtained in 85% total yield (34.86 g) as a yellow foam and a small portion was quantitatively converted to its dihydrochloride salt (4d) with 20% HCl in ethanol. Off-white solid, m.p. 161°-165° C. (dec.); $^1H$ NMR (D$_2$O) δ 8.70-8.62 (m, 1H), 8.46-8.41 (m, 1H), 8.37-8.29 (m, 1H), 8.04-8.00 (m, 1H), 7.88-7.81 (m, 2H), 4.29-4.26 (m, 1H), 3.86-3.51 (m, 2H), 3.44 and 3.42 (2s, 6H), 3.38-3.32 and 2.86-2.78 (2m, 1H), 3.00-2.96 (m, 2H), 2.49 and 2.21 (2m, 1H), 1.84-1.50 (m, 6H), 1.41-1.36 (m, 1H), 1.19-0.97 (m, 3H), 0.79-0.61 (m, 4H), 0.29-0.18 and 0.00- (−0.22) (2m, 1H); NMR (D$_2$O) ppm 168.79, 168.71, 139.85-119.54 (19 lines, olefinic), 66.09, 52.48, 52.17, 46.94, 46.16, 45.93, 2.96, 42.71, 39.10, 36.59, 36.48, 31.91, 31.68, 1.06, 30.67, 29.51, 29.39, 28.62, 27.96, 23.31, 3.22, 14.29, 10.50; IR (KBr, cm$^{-1}$) 3573-3390, 2933, 1631, 1144, 796, 590; MS m/z (MH$^+$-2HCl) calcd for $C_{24}H_{37}N_4O_3S$ 461.2586, obsd 461.2584.

EXAMPLE 4

Preparation of 1-[5-[(3-amino-1,2,5-thiadiazol-4-yl)amino]-2-[[[5-(dimethylamino)-1-naphthalenyl]sulfonyl]amino]-1-oxopentyl]-4-ethylpiperidine S-oxide (6d)

A suspension of free amine 4d (13.05 g, 0.028 mol) and 3-amino-4-methoxy-1,2,5-thiadiazole-I-oxide (12.5 g, 0.085 mmol) in methanol (55 mL) was stirred at ambient temperature for about 8 hours. At this time, an additional 10.5g of the thiadiazole-1-oxide was added. The suspension was stirred for a total of 48 hours before it was suction-filtered and concentrated. Purification of the residue by flash chromatography on silica gel (elution with ethyl acetate followed by 10% methanol in dichloromethane) afforded 10.89 g (78% based on recovered starting material) of 6d as a yellow foam, m.p. 158°-168° C. (decomposes at 173° C.); $^1H$ NMR (CDCl$_3$/DMSO-d$_6$) δ 8.47 (d, J=8.5 Hz, 1H), 8.30 (d, J=8.6 Hz, 1H), 8.15-7.49 (m, 6H), 7.18 (d, J=7.5 Hz, 1H), 4.11-3.88 (m, 2H), 3.52-3.48 (m, 1H), 3.34-3.26 (m, 3H), 2.84 (s, 6H), 2.77-1.88 (m, 2H), 1.69-1.34 (m, 6H), 1.17-0.98 (m, 3H), 0.83-0.76 (m, 4H), 0.24-0.12 (m, 1H); $^{13}C$ NMR (CDCl$_3$/DMSO-d$_6$) ppm 167.74, 167.64, 157.55, 157.32, 150.86, 135.42, 135.26, 129.51, 129.42, 128.92, 128.81, 128.21, 128.07, 127.37, 127.30, 122.67, 122.54, 119.02, 114.70, 114.57, 51.38, 51.26, 44.98, 44.78, 44.73, 44.55, 42.50, 42.36, 41.72, 41.20, 36.60, 31.59, 31.26, 30.57, 30.44, 29.76, 29.55, 28.14, 27.97, 23.76, 10.58; IR (KBr, cm$^{-1}$) 3375, 3237, 2937, 1614, 1583, 1149, 1064, 795, 629; MS m/z (MH$^+$) calcd for $C_{26}H_{38}N_7O_4S_2$ 576.2427, obsd 576.2441.

EXAMPLE 5

Preparation of
1-[5-[(2-amino-1,2-diiminoethyl)amino]-2-[[[5-(dimethylamino)-1-naphthalenyl]sulfonyl]amino]-1-oxopentyl]-4-ethylpiperidine trihydrochloride hydrate 17d)

Concentrated hydrochloric acid (6.1 mL) was added to a mixture of 6d (5.44 g, 9.48 mmol) in methanol (87 mL) at room temperature. The reaction mixture was stirred for about 3 hours before additional hydrochloric acid (1 mL) was added in order to complete the reaction. Evaporation of the solvent after about 7 hours gave 6.05 g (100%) of 7d as a pale-yellow solid, m.p. 175°-179° C. (decomposes at 192° C.); $^1$H NMR (D$_2$O) δ 8.77-8.69 (m, 1H), 8.52-8.46 (m, 1H), 8.38-15 8.31 (m, 1H), 8.15-8.11 (m, 1H), 7.95-7.86 (m, 2H), 4.34-4.25 (m, 1H), 3.76-3.60 (m, 2H), 3.53 (s, 6H), 3.42-3.35 (m, 1H), 2.91-2.27 (m, 1H), 1.94-1.54 (m, 5H), 1.43-1.39 (m, 1H), 1.21 and 0.99 (2m, 4H), 0.81-0.71 (m, 3H), 0.30-0.25 and −0.08-(−0.15) (2m, 1); $^{13}$C NMR (D$_2$O) ppm 171.98, 171.89, 159.38, 156.88, 142.07-123.03 (17 lines, olefinic), 60.83, 58.65, 55.70, 55.37, 50.32, 50.27, 49.42, 49.21, 46.44, 46.17, 45.96, 39.81, 39.69, 35.19, 34.92, 34.29, 33.91, 32.95, 32.81, 31.87, 31.21, 26.15, 26.06, 20.24, 13.76; IR (KBr, cm$^{-1}$) 3412, 2961, 1693, 1631, 1465, 1146, 797, 591; MS m/z (MH+-3HCl) calcd for C$_{26}$H$_{40}$N$_7$O$_3$S$_1$ 530.2913, obsd 530.2902.

EXAMPLE 6

Preparation of
1-[5-[(2-amino-1,2-diiminoethyl)amino]-2-[[[5-(dimethylamino)-1-naphthalenyl]sulfonyl]amino]-1-oxopentyl]-4-methylpiperidine trihydrochloride hydrate (7c)

For 3c: yellow foam, m.p. 70°-73° C. (dec.); $^1$H NMR (CDCl$_3$) δ 8.48 (d, J=8.5 Hz, 1H), 8.27 (t, J=8.7 Hz, 1H), 8.16 (d, J=7.3 HZ, 1H), 7.58-7.51 (m, 1H), 7.44-7.35 (m, 1H), 7.33 (s, 5H), 7.16-7.13 (m, 1H), 6.11 (d, J=8.1 Hz, 1H), 5.04 (s, 2H), 4.83-4.71 (m, 1H), 3.99-3.88 (m, 2H), 3.40-3.27 (m, 1H}, 3.17-2.93 (m, 2H), 2.81 (s, 6H), 2.68-1.94 (m, 2H), 1.57-1.29 (m, 8H), 0.81 and 0.73 (2d, J=6.1, 6.1 Hz, 3H), 0.17-0.10 (m, 1H); $^{13}$C NMR (CDCl$_3$) 168.55, 168.36, 156.43, 151.69, 136.65-115.43 (19 lines, olefinic), 66.56, 60.36, 52.30, 52.19, 45.64, 45.41, 45.37, 45.02, 42.79, 42.12, 40.34, 34.24, 33.91, 33.22, 30.79, 30.76, 30.63, 30.55, 25.14, 21.38, 21.24, 21.01, 14.17; IR (film, cm$^{-1}$) 3160, 2980, 2940, 1720, 1640, 1460, 1250, 1145, 795, 730; MS m/z (MH+) 581.

Anal Calcd for C6hd 31H$_{40}$N$_4$O$_5$S$_1$: C, 64.11; H, 6.94; N, 9.65.

Found C, 64.19; H, 7.0; N, 9.40.

For 4c: off-white solid, m.p. 107°-112° C. (dec.); $^1$H NMR (D$_2$O) δ 8.69 (dd, J=15.5, 8.8 Hz, 1H), 8.45 (m, 1H), 8.34 (m, 1H), 8.04 (m, 1H), 7.92-7.82 (m, 2H), 4.37-4.25 (m, 1H), 3.60-3.51 (m, 2H), 3.45 (2s, 6H), 3.35-3.31 and 2.88-2.80 (2m, 1H), 3.00 (br s, 2H), 2.52-2.40 and 2.33-2.25 (2m, 1H), 1.84-1.31 (m, 8H), 0.78-0.73 (m, 3H), 0.36-0.25 and 0.00-(−0.16) (2m, 1H); $^{13}$C NMR (D$_2$O) ppm 168.83, 168.74, 139.49-119.61 (19 lines, olefinic), 57.61, 52.52, 52.15, 46.99, 46.92, 46.07, 45.86, 42.91, 42.64, 39.08, 34.11, 34.05, 33.77, 33.18, 29.95, 29.74, 29.49, 29.40, 23.30, 23.22, 20.97, 20.41, 17.00; IR (KBr, cm$^{-1}$) 3580-3380, 2950, 1638, 1631, 1145, 795, 590; MS m/z (MH+-2HCl) calcd for C$_{23}$H$_{35}$N$_4$O$_3$S$_1$ 447.2430, obsd 447.2435.

For 6c: yellow solid, m.p. 138°-144° C. (dec.); $^1$H NMR (CDCl$_3$) δ 8.53-8.12 (m, 4H), 7.80 (br s, 1H), 7.61-7.14 (m, 5H), 4.26-3.90 (m, 1H), 3.68-3.37 (m, 2H), 3.18 (br s, 1H) 2.98 and 2.63 (2m, 1H), 2.84 (s, 6H), 2.33-2.26 (m, 1H), 2.05-1.30 (series of m, 7H), 0.93-0.79 (m, 3H), 0.50-0.46 and 0.14-0.10 (2m, 1H); $^{13}$C NMR (CDCl$_3$) ppm 168.52, 159.53, 158.87, 158.83, 158.67, 151.64, 151.53, 134.63-115.40 (21 lines, olefinic), 53.00, 52.38, 52.14, 46.19, 45.91, 45.49, 45.41, 45.38, 43.86, 43.60, 42.90, 42.80, 42.35, 41.97, 34.30, 33.97, 33.33, 33.19, 30.85, 30.77, 30.56, 24.11, 21.54, 21.33, 21.19; IR (KBr, cm$^{-1}$) 3350-3076, 2950, 1615, 1587, 1456, 1147, 1063, 794; MS m/z (MH+) calcd for C$_{25}$H$_{36}$N$_7$O$_4$S$_2$ 562.2270, obsd 562.2261.

For 7c: off-white solid, m.p. 175°-180° C. (dec.); $^1$H NMR (DMSO-d$_6$) δ 11.04 (br s, 1H), 10.43 (br s, 3H), 10.33 (br s, 2H), 8.9 (br s, 1H), 8.8 (br s, 1H), 8.52 (br s, 1H), 8.16 (d, 1H), 8.07 (d, 1H), 7.36 (br s, 1H), 4.22 (br m, 1H), 3.67 (br m, 2H), 3.32 (br m, 2H), 3.03 (d, 6H), 2.72-2.40 (br m, 1H), 2.20-1.80 (br m, 1H), 1.60-1.10 (m, 9H), 0.70 (d, 3H); $^{13}$C NMR (DMSO-d$_6$) ppm 167.94, 156.18, 153.06, 136.64, 128.97, 128.71, 128.44, 127.40, 126.90, 124.91, 123.60, 117.93, 117.71, 64.05, 54.87, 52.04, 45.80, 45.71, 44.63, 42.50, 41.60, 33.70, 32.87, 30.16, 30.05, 23.21, 21.41, 13.53; IR (KBr, cm$^{-1}$) 3400, 2950, 1680, 1635, 1460.

EXAMPLE 7

Preparation of
1-[5-[(2-amino-1,2-diiminoethyl)amino]-2-[[[5-(dimethylamino)-1-naphthalenyl]sulfonyl]amino]-1-oxopentyl]morpholine trihydrochloride hydrate (7e)

For 3e: yellow foam, m.p. 65°-68° C. (dec.); $^1$H NMR (CDCl$_3$) δ 8.54 (d, J=8.4 Hz, 1H), 8.29 (d, J=8.6 Hz, 1H), 8.18 (d, J=7.2 Hz, 1H), 7.58-7.55 (m, 1H), 7.53-7.45 (m, 1H), 7.33 (s, 5H), 7.17 (d, J=7.5 Hz, 1H), 6.05 (d, J=8.7 Hz, 1H), 5.02 (s, 2H), 4.81 (br s, 1H), 4.05 (m, 1H), 3.36-3.32 (m, 2H), 3.08-2.91 (m, 8H), 2.84 (s, 6H), 1.53-1.34 (m, 4H); $^{13}$C NMR (CDCl$_3$) ppm 169.24, 162.49, 156.47, 151.35, 136.58, 134.93, 130.61, 129.68, 129.37, 128.49, 128.24, 128.08, 127.92, 123.10, 119.47, 115.66, 66.59, 66.27, 66.15, 51.84, 45.54, 45.44, 45.34, 42.29, 39.95, 36.37, 1715, 1641, 1249, 1144, 1113, 794 626 574; MS m/z (MH+) 569.

Anal. Calcd for C$_{28}$H$_{36}$N$_4$O$_6$S$_1$: C, 61.25; H, 6.38; N, 9.85.

Found: C, 60.83; H, 6.59; N, 9.84.

For 4e: off-white solid, m.p. 169°-176° C. (dec.); $^1$H NMR (D$_2$O) δ 8.67 (d, J=8.8 Hz, 1H), 8.44 (d, J=8.7 Hz, 1H), 8.30 (d, J=7.4 Hz, 1H), 8.08 (d, J=7.8 Hz, 1H), 7.90-7.82 (m, 2H), 4.25-4.21 (m, 1H), 3.49 (s, 6H), 3.43-2.91 (m, 8H), 2.71-2.66 (m, 1H), 1.84-1.73 (m, 1H), 1.68-1.53 (m, 3H); $^{13}$C NMR (D$_2$O) ppm 171.41, 140.32, 136.76, 132.94, 130.69, 130.16, 128.97, 128.62, 128.16, 127.31, 121.76, 67.91, 67.82, 59.41, 53.93, 48.82, 47.48, 44.00, 40.79, 30.91, 25.02, 18.78; IR (KBr, cm$^{-1}$) 3600-3300, 2950, 1650, 1480, 1150, 800; MS m/z (MH+-2HCl) calcd for C$_{21}$H$_{31}$N$_4$O$_4$S$_1$ 435.2066, obsd 435.2061.

For 6e: yellow solid, m.p. 152°-155° C. (dec.); $^1$H NMR (CDCl$_3$)δ 8.53 (d, J=8.4 Hz, 1H), 8.43-8.15 (m, 3H), 7.59-7.47 (m, 3H), 7.19-7.16 (m, 2H), 7.81 and 6.81 (2br s, 1H), 4.23-4.13 (m, 1H), 3.66-3.01 (m, 9H), 2.86 and 2.84 (2s, 6H), 1.83-1.40 (m, 5H); $^{13}$C NMR (CDCl$_3$) ppm 170.01, 169.38, 159.43, 158.90, 158.77, 158.66, 151.11, 135.10, 134.86, 130.43, 129.65, 129.55, 129.21, 128.49, 123.21, 119.48, 115.97, 115.68, 66.23, 53.47, 52.44, 52.04, 45.85, 45.58, 45.53, 43.81, 43.52, 42.25, 30.44, 29.70, 24.08; IR (KBr, cm$^{-1}$) 3600-3080, 2942, 2867, 1616, 1587, 1148, 1115, 1065, 628; MS m/z (MH+) calcd for $C_{28}H_{32}N_2O_5S_2$ 550.1906, obsd 550.1892.

For 7e: white solid, m.p. 183°–185° C. (decomposes at 191° C.); $^1$H NMR (D$_2$O) δ 8.65–8.62 (m, 1H), 8.46–8.40 (m, 1H), 8.29–8.22 (m, 1H), 8.07–8.02 (m, 1H), 7.89–7.78 (m, 2H), 4.26–4.11 (m, 1H), 3.48 (s, 6H), 3.43–2.64 (series of m, 10H), 1.87–1.45 (m, 4H); $^{13}$C NMR (D$_2$O) ppm 172.24, 171.67, 171.43, 161.28, 160.34, 157.99, 155.51, 140.70, 140.64, 136.75, 136.70, 132.95, 130.68, 130.23, 128.95, 128.44, 128.33, 127.39, 121.74, 121.62, 67.95, 67.84, 59.45, 57.23, 53.97, 50.93, 48.85, 47.55, 45.01, 44.90, 44.21, 44.03, 31.23, 30.87, 25.37, 24.68, 18.85; IR (KBr, cm$^{-1}$) 3408, 3202–2974, 1693, 1637, 1466, 1440, 1148, 1113, 795, 591; MS m/z (MH+·3HCl) calcd for $C_{23}H_{34}N_7O_4S_1$ 504.2393, obsd 504.2389.

EXAMPLE 8

Preparation of 1-[5-(2-amino-1,2-diiminoethyl)amino]-2-[[[5-(dimethylamino)-1-naphthalenyl]sulfonyl]amino]-1-oxopentyl]homopiperidine trihydrochloride hydrate (7g)

For 3g: yellow foam, m.p. 45°–50° C. (closed tube); $^1$H NMR (CDCl$_3$) δ 8.47 (d, J=8.5 Hz, 1H), 8.25 (d, J=8.7 Hz, 1H), 8.18 (d, J=7.3 Hz, 1H), 7.59–7.54 (m, 1H), 7.42–7.35 (m, 1H), 7.35 (s, 5H), 7.16 (d, J=7.6 Hz, 1H), 6.15 (d, J=8.2 HZ, 1H), 5.05 (s, 2H), 4.76 (m, 1H), 3.98–3.91 (m, 1H), 3.39–3.31 (m, 1H), 3.19–3.02 (m, 3H), 2.95–2.86 (m, 1H), 2.82 (s, 6H), 2.73–2.64 (m, 1H), 1.62–0.85 (series of m, 12H); $^{13}$C NMR (CDCl$_3$) ppm 169.99, 156.37, 151.71, 136.62, 134.85, 130.51, 129.90, 129.56, 129.35, 128.48, 128.02, 122.89, 119.27, 115.57, 66.60, 52.60, 47.27, 46.02, 45.36, 40.45, 31.13, 28.67, 26.84, 26.67, 26.10, 25.19; IR (KBr, cm$^-$) 3300, 2970, 1725, 1640, 1460, 1250, 1150, 795, 630; MS m/z (MH+) 473;

Anal. Calcd for $C_{31}H_{40}N_4O_5S_1$:
C, 64.12; H, 6.95; N, 9.65.
Found: C, 64.03; H, 7.06; N, 9.40.

For 4g: off-white solid, m.p. 164°–170° C. (dec.); $^1$H NMR (D$_2$O) δ 8.61 (d, J=8.7 Hz, 1H), 8.40 (d, J=8.6 Hz, 1H), 8.30 (d, J=7.4 Hz, 1H), 8.00 (d, J=7.8 Hz, 1H), 7.83–7.78 (m, 2H), 4.14–4.09 (m, 1H), 3.42 (s, 6H), 3.09–2.86 (m, 5H), 2.58–2.50 (m, 1H), 1.87–1.55 (m, 4H), 1.50–1.39 (m, 1H), 1.22–1.11 (m, 5H), 0.91–0.73 (m, 3H); $^{13}$C NMR (D$_2$O) ppm 154.17, 123.05, 118.49, 115.05, 112.46, 112.09, 110.77, 110.32, 110.07, 109.52, 103.46, 36.30, 31.77, 30.63, 30.00, 22.82, 13.41, 11.86, 10.03, 9.96, 9.26, 7.05; IR (KBr, cm$^{-1}$) 3425, 2929, 1631, 1473, 1432, 1142, 797, 590; MS m/Z (MH+·2HCl) calcd for $C_{23}H_{35}N_4O_3S_1$ 447.2430, obsd 447.2436.

For 6g: yellow solid, m.p. 148°–152° C. (dec.); $^1$H NMR (CDCl$_3$) δ 8.50–8.16 (m, 4H), 7.85 and 7.11 (2m, 1H), 7.58–7.43 (m, 4H), 7.24–7.16 (m, 1H), 4.10 (m, 1H), 3.55 (m, 1H), 3.41–3.09 (m, 4H), 2.85 (s, 6H), 2.74–2.62 (m, 1H), 2.03–1.90 (m, 1H), 1.75–0.96 (series of m, 11H); $^{13}$C NMR (CDCl$_3$) ppm 170.95, 170.38, 159.44, 158.85, 158.66, 151.00, 135.38, 134.88, 130.40, 130.17, 129.63, 129.57, 129.47, 129.10, 128.44, 128.31, 123.13, 119.93, 119.62, 115.90, 115.60, 53.47, 53.13, 52.93, 47.76, 47.66, 46.17, 45.95, 45.53, 45.50, 43.89, 43.74, 30.83, 30.09, 28.57, 27.05, 26.82, 26.67, 26.40, 26.09, 24.21, 24.10; IR (KBr, cm$^{-1}$) 3500–3200, 2935, 1615, 1587, 1147, 1064, 794, 627; MS m/z (MH+) calcd for $C_{25}H_{36}N_7O_4S_2$ 562.2270, obsd 562.2258.

For 7g: white solid, m.p. 181°–183° C. (decomposes at 191° C.); $^1$H NMR (D$_2$O) δ 8.55 (d, J=8.7 Hz, 1H), 8.40 (d, J=8.7 Hz, 1H), 8.20 (d, J=7.3 Hz, 1H), 8.03 (d, J=7.8 Hz, 1H), 7.81–7.75 (m, 2H), 4.11–4.06 (m, 1H), 3.45 (s, 6H), 3.08–3.04 (m, 2H), 2.90–2.83 (m, 1H), 2.54–2.47 (m, 1H), 1.91–1.61 (m, 4H), 1.41–1.37 (m, 1H), 1.16–1.11 (m, 4H), 0.89–0.72 (m, 3H); $^{13}$C NMR (D$_2$O) ppm 170.44, 156.20, 153.68, 138.79, 134.86, 131.32, 128.68, 128.43, 127.24, 126.69, 126.50 125.59, 120.01, 52.66, 48.09, 47.18, 46.13, 43.36, 29.96, 28.17, 26.35, 26.27, 25.62, 22.98, 17.18; IR (KBr, cm$^{-1}$) 3407, 3300–2934, 1692, 1626, 1466, 1441, 1147, 796, 591; MS m/z (MH+·3HCl) calcd for $C_{25}H_{38}N_7O_3S_1$ 516.2757, obsd 516.2753.

EXAMPLE 9

Preparation of ethyl N-[5-[(2-amino-1,2-diiminoethyl)amino]-2-[[[5-(dimethylamino)-1-naphthalenyl]sulfonyl]amino]-1-oxopentyl]-N-butylglycinate trihydrochloride hydrate (7f)

For 3f: yellow foam, m.p. 45°–49° C.; $^1$H NMR (MeOH-d$_4$) δ 8:56–8:52 (m, 1H), 8.37–8.33 (m, 1H), 8.23–8.17 (m, 1H), 7.58–7.50 (m, 2H), 7.32–7.31 (m 5H), 7.26–7.22 (m, 1H), 5.02 (s, 2H), 4.87 (s, 3H), 4.61–3.29 (series of m, 5H), 3.17–2.95 (m, 3H), 2.84 (s, 6H), 2.06–1.93 (m, 1H), 1.56–1.31 (m, 6H), 1.25–1.04 (m, 6H), 0.90–0.76 (m, 1H); $^{13}$C NMR (MeOH-d$_4$) ppm 173.77, 172.97, 172.09, 171.09, 170.68, 159.02, 153.38, 153.28, 137.44–116.65 (22 lines, olefinic), 67.57, 63.10, 62.67, 62.45, 54.29, 53.86, 53,62, 53.45, 50.66, 46.12, 44.78, 44.56, 41.06, 40.89, 32.18, 31.58, 31.37, 31.09, 30.65, 30.25, 27.27, 26.80, 26.56, 26.01, 25.59, 21.95, 21.80, 21.16, 14.76, 14.72, 14.48, 14.42; IR (KBr, cm$^{-1}$) 3422, 2943, 1724, 1644, 1250, 1146, 1026, 793, 614; MS m/z (MH+) 641;

Anal. Calcd for $C_{33}H_{44}N_4O_7S_1$:
C, 61.86; H, 6.93; N, 8.75.
Found C, 62.12; H, 6.77; N, 8.77.

For 4f: off-white solid, m.p. 138°–142° C. (dec.); $^1$H NMR (D$_2$O) δ 8.64–8.56 (m, 1H), 8.42 (d, J=8.0 Hz, 1H), 8.29–8.21 (m, 1H), 7.99 (d, J=7.8 Hz, 1H), 7.87–7.77 (m, 2H), 4.61–3.94 (series of m, 4H), 3.66–3.48 (m, 1H), 3.43 and 3.42 (2s, 6H), 3.04–2.80 (m, 3H), 2.01–1.37 (m, 6H), 1.21–1.07 (m, 6H), 0.88–0.61 (m, 2H); $^{13}$C NMR (D$_2$O) ppm 172.29, 172.06, 171.62, 171.06, 170.88, 170.56, 139.76–119.63 (23 lines, olefinic), 63.27, 63.13, 62.84, 62.48, 62.34, 53.72, 53.16, 52.78, 52.55, 52.47, 52.26, 49.29, 48.76, 47.95, 46.99, 43.90, 43.46, 40.45, 39.13, 30.25, 30.04, 29.69, 29.34, 28.85, 28.20, 26.18, 25.65, 24.51, 24.15, 23.94, 23.31, 23.19, 19.97, 19.76, 19.35, 17.09, 13.49, 13.24, 13.11; IR (KBr, cm$^{-1}$) 3433, 2958, 1734, 1641, 1468, 1144, 797, 592; MS m/z (MH+) calcd for $C_{25}H_{39}N_4O_5S_1$ 507,2641, obsd 507.2632.

For 6F: yellow foam, m.p. 119°–124° C. (dec.); $^1$H NMR (CDCl$_3$) δ 8.51–8.47 (m, 1H), 8.39–8.24 (m, 1H), 8.20–8.13 (m, 2H), 7.78 and 6.68 (2br s, 1H), 7.40–6.98 (m, 4H), 5.02–3.87 (series of m, 4H), 3.77–2.95 (m, 4H), 2.83 (2s, 6H), 2.13–1.79 (m, 4H), 1.79–1.47 (m, 5H), 1.25–1.07 (m, 6H), 0.92–0.77 (m, 2H); $^{13}$C NMR (D$_2$O) pp, 171.17, 170.97, 170.44, 170.23, 170.09, 169.88, 159.18, 158.75, 158.64, 158.52, 158.40, 151.45, 135.30–114.94 (26 lines, olefinic), 61.82, 61.28, 60.89, 60.20, 52.96, 52.68, 52.55, 52.46, 52.04, 51.90, 48.83, 48.53, 47.59, 45.25, 43.95, 43.64, 43.44, 43.09, 42.94, 30.47, 30.34, 29.48, 29.27, 28.77, 26.54, 26.35, 25.75, 24.79, 24.51, 24.19, 23.87, 23.63, 20.84, 20.48, 20.37, 19.70, 19.64, 14.01, 13.95, 13.87, 13.55, 13.43, IR (KBr, cm$^{-1}$) 3357, 3270, 2944, 1737, 1616, 1585, 1164, 1147, 1063, 795, 628; MS m/z (MH+) calcd for $C_{27}H_{40}N_7O_6S_2$ 622.2482, obsd 622.2485.

For 7F: off-white solid, m.p. 173°–176° C. (decomposes at 183° C.); ¹H NMR (D₂O) δ 8.73–8.66 (m, 1H), 8.43–8.36 (m, 2H), 8.01 (d, J=7.8 Hz, 1H), 7.93–7.83 (m, 2H), 4.58–3.93 (series of m, 4H), 3.57–3.37 (m, 3H), 3.42 (s, 6H), 3.03–2.87 (m, 1H), 1.92–1.46 (m, 6H), 1.19–1.04 (m, 6H), 1.04–0.63 (m, 2H); ¹³C NMR (D₂O) ppm 171.60, 171.08, 170.22, 170.35, 169.86, 153.03, 138.48–118.94 (30 lines, olefinc), 62.15 61.79, 61.76, 61.62, 56.99, 52.10, 52.01, 51.89, 51.76, 46.43, 46.26, 42.81, 42.76, 42.62, 29.55, 29.28, 28.44, 24.95, 23.44, 22.25, 22.12, 22.06, 19.09, 19.03, 18.65, 16.43, 12.85, 12.58; IR (KBr, cm⁻¹) 3422, 3119, 2958, 1693, 1637, 1412, 1146, 795, 592; MS m/z (MH⁺) calcd for C₂₇H₄₂N₇O₅S₁ 576.2968, obsd 576.2959.

EXAMPLE 10

Preparation of
1-[5-[(2-amino-1,2-diiminoethyl)amino]-2-[[[5-(dimethylamino)-1-naphthalene]amino]-1-oxopentyl]piperidine hydrochloride (7a)

For 3a: yellow foam, m.p. - ° C. (dec.); ¹H NMR (CDCl₃) δ 8.46 (d, 1H), 8.26 (d, 1H), 7.75 (t, 1H), 7.40 (t, 1H), 7.31 (s, 5H), 7.13 (d, 1H), 6.14 (d, 1H), 5.02 (s, 2H), 4.80 (m, 1H), 4.00 (m, 1H), 3.25–2.80 (m, 12H), 1.60–1.20 (m, 8H), 0.80 (m, 2H); ¹³C NMR (CDCl₃) ppm 169.15, 157.12, 152.39, 137.22, 135.26, 131.11, 130.34, 130.21, 129.96, 129.11, 129.07, 128.68, 128.63, 123.56, 119.83, 116.07, 66.92, 52.53, 46.44, 45.70, 40.50, 30.91, 26.18, 25.35, 25.28, 24.29; MS m/z (MH⁺) 567.

For 4a: yellow foam, m.p. 63°–70° C. (dec.); ¹H NMR (CDCl₃/D₂O) δ 8.47 (d, 1H), 8.28 (d, 1H), 8.15 (d, 1H), 7.55 (t, 1H), 7.49 (t, 1H), 7.15 (d, 1H), 4.05 (m, 1H), 2.55 (m, 2H), 1.60–1.20 (m, 1H), 3.25–2.80 (m, 12H), 2.55 (m, 2H), 1.60–1.20 (m, 8H), 1.00–0.80 (m, 2H); 13C NMR (CDCl₃) ppm 168.58, 151.56, 135.17, 130.31, 129.75, 129.69, 129.02, 128.31, 122.88, 119.37, 115.42, 52.52, 46.22, 45.40 43.17, 41.61, 31.17, 28.60, 26.04, 25.12, 24.15; IR (KBr, cm⁻¹) 3400, 3280, 2960, 2850, 1735, 1640, 1590, 1580, 1450, 1320, 1170, 1150, MS m/z (MH⁺) 432.

Anal. Calcd for C₂₁H₃₂N₄O₃S₁ 0.3 H₂O:
C, 59.21; H, 7.71; N, 13.15.
Found: C, 59.85; H, 7.43; N, 12.83.

For 6a: ¹H NMR (CDCl₃) δ 8.50–8.10 (m, 3H) 7.57–7.40 (m, 2H), 7.15 (m, 1H), 4.21–4.13 (bs, 1H), 3.72 (bs, 1H), 3.14 (bm, 6H), 1.59–1.46 (bm, 8H); IR (KBr, cm⁻¹) 3350–3050, 2945, 1615, 1580, 1455, 1145, 1065; MS m/z (MH⁺) 549;

For 7a: off-white solid, m.p. 198°–202° C. (dec); ¹H NMR (CDCl₃) δ 8.70 (d, 1H); 8.40 (d, 1H), 7.84 (d, 1H), 7.54 (d, 1H), 7.38–7.20 (m, 3H), 3.68 (bs, 2H) 3 10–2.70 (m, 6H), 2.49 (bm, 1H), 1.36–0.60 (m, 10H); ¹³C NMR (CDCl₃) ppm 167.8, 156.1, 152.3, 136.1, 129, 128.9, 127.7, 127.1, 126.0 125.2, 118.7, 56.6, 52.1, 46.3, 42.6, 29.3, 25.7, 24.7, 23.5, 23.0, 22.8, 18.0; IR (KBr, cm⁻¹) 3400–3000, 2950, 1710, 1635, 1480, 1460, 1160; MS m/z (MH⁺) 501;

Anal. Calcd for C₂₄H₃₅N₇O₇S₁ 3HCl H₂O EtOH:
C, 46.26; H, 6.87; N, 14.52.
Found: C, 46.16; H, 7.09; N, 14.55.

EXAMPLE 11

Preparation of
1-[5-[2-(amino-1,2-diiminoethyl)amino]-2-[[(4-methylphenyl)sulfonyl]amino]-1-oxopentyl]-4-methylpiperidine hydrochloride (7I)

For 3I: white foam, ¹H NMR (CDCl₃) δ 7.7 (m, 2H), 7.2 (m, 2H), 5.9–5.7 (d, 1H), 5.2 (s, 2H), 4.9 (m, 1H), 4.3–3.9 (m, 2H), 3.5–3.2 (m, 3H), 2.8–2.5 (m, 1H), 2.35 (s, 3H), 2.4–2.2 (m, 1H), 1.8–1.4 (m, 8H), 0.9 (d, 3H), 0.4 (m, 1H); ¹³C NMR (CDCl₃) ppm 168.43, 156.45, 143.26, 136.60, 136.32, 129.59, 129.31, 128.48, 128.04, 128.01, 127.66, 127.32, 66.58, 52.32, 52.21, 45.54, 45.05, 42.91, 42.20, 40.39, 34.15, 33.90, 33.35, 3.21, 30.81, 30.72, 30.52, 25.25, 21.57, 21.46, 21.17; IR (KBr, cm⁻¹) 3350, 3250, 2945, 1720, 1640, 1440; MS m/z (MH⁺) calcd for C₂₆H₃₆N₃O₅S 502.2376, obsd 502.2367.

For 4I: white crystals, m.p. ° C. (dec.); ¹H NMR (CDCl₃) δ 9.2–8.2 (bm, 3H), 7.73 (m, 2H), 7.23 (m, 2H), 4.3–2.8 (m, 7H), 2.4 (s, 3H), 2.0–1.2 (m, 8H), 0.8 (d, 3H), 0.4 (m, 1H); ¹³C NMR (CDCl)₃ ppm 168.33, 143.20, 136.59, 129.57, 129.32, 127.55, 127.19, 52.33, 45.31, 42.25, 39.07, 34.91, 33.52, 33.34, 33.21, 30.62, 30.46, 30.08, 23.76, 21.60, 21.47, 21.08; IR (film, cm⁻¹) 3600–2975, 1645, 1180; MS m/z (MH⁺) 367.

Anal. Calcd for C₁₈H₂₉N₃O₃S₁ HCl H₂O:
C, 511.23; H, 7.64.
Found: C, 51.47; H, 7.06.

For 6I: off-white foam, ¹H NMR (CDCl₃) δ 7.64 (m, 2H), 7.17 (m, 2H), 4.13 (m, 2H), 3.6–3.18 (m, 2H), 2.8–2.6 (m, 2H), 2.3 (s, 4H), 2.1 (s, 3H), 1.6–1.4 (m, 9H), 0.40 (d, 3H), 0.33 (m, 1H); ¹³C NMR (CDCl₃) ppm 68.95, 168.72, 159.46, 158.82, 143.22, 136.78, 29.60, 129.32, 127.60, 127.33, 52.74, 52.64, 45.72, 45.21, 42.95, 42.24, 41.72, 34.30, 34.06, 33.44, 31 32, 30.97, 30.90, 28.64, 21.69, 21.35; IR (KBr, cm⁻¹) 3300, 2950, 1640, 1160; MS m/z (MH⁺) calcd for C₂₀H₃₁N₆O₄S₂ 483.1848, obsd 483.1842.

For 7I: off-white crystals, m.p. 155°–160° C. (dec.); ¹H NMR (CDCl₃) δ 8.13 (bs, 1H), 7.69 (bs, 2H), 7.24 (bs, 2H), 4.50–4.46 (m, 2H), 3.70–3.50 (bm, 2H), 3.1 (bs, 2H), 2.89 (bs, 1H), 2.57 (s, 3H), 2.2–1.3 (m, 8H), 0.83 (bs, 3H), 0.4 (bs, 1H); IR (KBr, cm⁻¹) 3400–2950, 1700, 1640, 1480, 1190; MS m/z (MH⁺) 437.

EXAMPLE 12

For 3n: white foam, ¹H NMR (CDCl₃) δ 8.36 (s, 1H), 8.08–7.68 (m, 4H), 7.58–7.51 (m, 3H), 7.23 (s, 5H), 6.65 (bs, 1H), 5.24 (bm, 1H), 5.0 (s, 2H), 4.81 (bm, 1H), 3.65 (m, 2H), 3.50–3.26 (m, 6H), 3.02 (m, 2H), 2.49 (m, 1H), 1.51–1.02 (m, 1OH); ¹³C MR (CDCl₃) ppm 169.14, 167.62, 156.40, 136.52, 135.99, 134.67, 131.91, 129.38, 129.14, 128.69, 128.44, 128.32, 127.86, 127.70, 127.38, 122.25, 66.38, 48.53, 46.48, 46.34, 45.58, 44.55, 43.26, 42.51, 40.40, 36.66, 33.20, 29.83, 26.22, 25.49, 25.37, 25.08, 24.82, 24.43 24.17; IR (KBr, cm⁻¹) 3300, 2980, 1720, 1640, 1540, 1450, 1180; MS m/z (MH⁺) 581.

Anal. Calcd for C₃₀N₃₆N₄O₆S:
C, 61.38; H, 6.3; N, 9.54.
Found: C, 60.85; H, 6.36; N, 9.62.

For 6n: white foam, ¹H NMR (CDCl₃) δ 8.37 (s, 1H), 8.01–7.48 (m, 10H), 4.83 (bs, 1H), 3.71–3.41 (bm, 9H), 2.2 (bs, 1H), 1.6–1.2 (bm, 10H); ¹³C NMR (CDCl₃/DMSO-d₆) ppm 169.24, 169.04, 168.38, 168.12, 158.93, 158.69, 158.20, 158.16, 136.34, 136.26, 134.75, 132.04, 129.40, 129.21, 128.74, 128.39, 127.79, 127.44, 122.35, 48.65, 48.45, 46.62, 46.56, 45.66, 43.84, 43.33, 30.24, 29.90, 26.31, 25.43, 24.23, 23.84, 23.65; IR (KBr, cm⁻¹) 3390, 3300, 2980, 1680, 1635, 1595; MS m/z (MH⁺) 562.

Anal. Calcd for C₂₄H₃₁N₇O₄S₁ H₂O: C, 49.73; H, 5.7; N, 16.91. Found: C, 49.28; H, 5.60, N, 17.64.

For 7n: white foam, m.p. 160°–165° C. (dec.); ¹H NMR (CDCl₃) δ 10.69 (bs, 1H), 10.14 (bs, 3H), 9.58 (bs, 1H), 9.58 (bs, 2H), 8.06 (s, 1H), 7.63–7.4 (m, 5H), 7.25

(bs, 1H), 4.65 (bs, 1H), 3.65 (bs, 1H), 3.4-3.0 (m, 9H), 1.40-1.0 (m, 10H); $^{13}$C NMR (CDCl$_3$/DMSO-d$_6$) ppm 168.71, 168.02, 156.69, 156.29, 157.68, 150.68, 136.42, 134.40, 131.72, 129.22, 128.99, 128.40, 127.91, 127.61, 127.24, 122.28, 65.41, 54.77, 51.88, 48.38, 46.33, 45.56, 43.44, 43.03, 28,32, 29.20, 26.11, 25.29, 24.08, 23.04, 22.87, 15.08; IR (film, cm$^{-1}$) 3200-2950, 1700, 1640, 1180; MS m/z (MH+) 516.

Anal. Calcd for C$_{24}$H$_{33}$N$_7$O$_4$S$_1$ 2HCl 3H$_2$O: C, 44.86; H, 6.43; N, 15.26. Found: C, 44.45; H, 5.85; N, 15.83.

EXAMPLE 13

For 2j: white foam, $^1$H NMR (CDCl$_3$) δ 7.65 (d, 2H), 7.4 (s, 5H), 7.2 (d, 2H), 5.8 (d, 1H), 5.4 (m, 1H), 5.05 (s, 2H), 3.7 (m, 1H), 3.0 (m, 2H), 2.3 (s, 3H), 1.7-1.4 (m, 5H); $^{13}$C NMR (CDCl$_3$) ppm 173.32, 156.52, 143.26, 137.06, 136.67, 129.71, 129.54, 128.42, 127.96, 127.10, 126.44, 125.93, 66.96, 66.40, 55.17, 40.20, 30.10, 25.27, 21.61, 21.42; IR (KBr, cm$^{-1}$) 3400, 3300, 2950, 1750, 1680, 1550, 1460; MS m/z (MH+) 421.

Anal. Calcd. for C$_{20}$H$_{24}$O$_5$N$_3$S$_1$: C, 57.14, 5.75; N, 6.66. Found: C, 57.20; H, 5.77; N, 6.56.

For 3j: colorless foam, $^1$H NMR (CDCl$_3$) δ 7.81 (d, 2H), 7.26-7.12 (m, 7H), 5.9 (d, 1H), 5.10 (m, 1H), 4.99 (2H), 3.52 (m, 1H), 3.4-2.9 (m, 6H), 2.29 (s, 3H), 1.65-0.9 (m, 10H); $^{13}$NMR (CDCl$_3$) ppm 168.42, 156.34, 143.22, 136.41, 136.23, 129.29, 128.30, 127.83, 127.31, 66.35, 52.16, 45.95, 43.17, 40.14, 30.50, 25.79, 25.20, 24.57, 23.97, 21.25; IR (KBr, cm$^{-1}$) 3300, 2950, 1740, 1650; MS m/z (MH+) 488.

Anal. Calcd. for C$_{25}$H$_{30}$O$_5$N$_3$S$_1$: C, 61.58; H, 6.82; N, 8.62. Found: C, 61.25; H, 6.90; N, 8.79.

For 6j: $^{13}$C NMR (CDCl$_3$) ppm 169.89, 168.84, 143.30, 139.62, 136.73, 129.7, 127.31, 123.31, 53.22, 52.61, 46.21, 43.27, 41.79, 41.53, 31.73, 28.58, 28.42, 25.95, 25.44, 25.12, 24.17, 24.07, 21.49, 20.71; IR (film, cm$^{-1}$) 3250, 2960, 1640, 1340, 1180; MS m/z (MH+) 354.

For 7j: white crystals, m.p. 145°-150° C. (dec.); $^1$H NMR (DMSO-d$_6$ δ 11.05 (bs, 1H), 10.58 (bs, 1H), 10.40 (bs, 2H), 10.05 (bs, 1H), 7.65 (m, 2H), 7.4 (m, 2H), 4.2 (m 2H), 3.4 (m, 3H), 3.0 (m, 1H), 2.5 (s, 3H), 1.9-1.2 (m, 6H); $^{13}$C NMR (D$_2$O) ppm 153.25, 140.0, 137.5, 129.4, 110.43, 114.07, 111.14, 39.24, 36.14, 30.82, 27.76, 27.04, 13.57, 9.73, 8.88, 7.38, 6.77, 4.70; IR (KBr, cm$^{-1}$) 3400-2980, 1700, 1640, 1410, 1160; MS m/z (MH+) 423.

EXAMPLE 14

Preparation of 2-[[(4-methylphenyl)sulfonyl]amino]-6-[[(phenylmethoxy)carbonyl]amino]hexanoic acid (2k)

N$^ε$-Carbobenzyloxy-L-lysine (30.0 g, 0.107 mmol) was dissolved in a solution of 2N NaOH (60 mL) and dioxane (150 mL) under nitrogen. After about 15 minutes at room temperature, the mixture was cooled to about 0° C. and subsequently treated with additional 2N NaOH (60 mL) and p-toluenesulfonyl chloride (20.4 g, 0.107 mmol) in 5 g portions over about 15 minutes. The mixture was stirred at about 0° C. for about 1 hour and at room temperature for about 18 hours before it was neutralized to pH 6 with 1N HCl. The mixture was then diluted with ethyl acetate and the organic phase was separated and washed with brine. The aqueous phase was extracted twice more with ethyl acetate and the combined organic phases were treated further as mentioned above. Following drying and solvent evaporation of the combined organic phases, the residue was first pre-columned on silica gel (elution with 10% methanol in dichloromethane) and subsequently recrystallized from ethyl acetate/hexanes (2:1) to give 37.67 g (81%) of the title compound as a white solid, m.p. 120°-121° C.; $^1$H NMR (CDCl$_3$) δ 8.37 (v br s, 0.5H), 7.71 (d, J=8.0 Hz, 2H), 7.32 (s, 5H), 7.23 (d, J=7.6 Hz, 2H), 6.49 and 4.89 (2m, 1H), 5.73 (d, J=8.4 Hz, 1H), 5.10 and 5.04 (2s, 2H), 3.91 (m, 1H), 3.17-3.02 (m, 2H), 2.35 (s, 3H), 1.73-1.66 (m, 2H), 1.40-1.24 (m, 4H); $^{13}$C NMR (CDCl$_3$) ppm 199.88, 175.06, 174.57, 158.37, 156.89, 143.66, 136.86, 136.32, 129.66, 128.54, 128.10, 127.19, 67.47, 66.89, 55.28, 40.95, 40.44, 32.25, 29.10, 28.75, 21.77, 21.46; IR (KBr, cm$^{-1}$) 3382, 3264, 2950, 1738, 1656 1550, 1334, 1286, 1160, 1092, 818, 678, 568; MS m/z (MH+) 435.1590, obsd 435.1595.

Anal. Calcd for C$_{21}$H$_{26}$N$_2$O$_6$S: C, 58.05; H, 6.03; N, 6.45. Found: C, 58.12; H, 6.03; N, 6.43.

EXAMPLE 15

Preparation of phenylmethyl [6-[1-piperidinyl]-5-[[(4-methylphenyl)sulfony]amino]-6-oxohexyl]carbamate (3k)

To a cold (0° C.), nitrogen-blanketed mixture of 2-[[(4-methylphenyl)sulfonyl]amino]-6-[[(phenylmethoxy)carbonyl]amino]hexanoic acid (18.00 g, 44.43 mmol), triethylamine (5.80 mL, 41.43 mmol) and piperidine (4.10 mL, 41.43 mmol) in anhydrous dimethylformamide (80 mL) was added dropwise diphenylphosphoryl azide (8.90 mL, 41.43 mmol). The mixture was stirred at about 0° C. for about 1 hour and at ambient temperature for about 2 hours before it was partitioned between ethyl acetate and water. The organic phase was separated and the aqueous phase was extracted three additional times with ethyl acetate. The combined extracts were then washed with saturated sodium bicarbonate solution, 1N hydrochloric acid and brine prior to drying and solvent concentration. There was isolated in sufficiently pure state 20.90 g (100%) of the title compound of as pale yellow oil; $^1$H NMR (CDCl$_3$) δ 7.62 (d, J=8.2 Hz, 2H), 7.30-7.22 (m, 5H), 7.19 (d, J=8.1 Hz, 2H), 5.94 (d, J=8.9 Hz, 1H), 5.09-5.07 (m, 1H), 5.03 (s, 2H), 3.90-3.88 (m, 1H), 3.43-3.36 (m, 1H), 3.09-2.91 (m, 5H), 2.32 (s, 3H), 1.4-1.23 (m, 10H), 1.09-0.97 (m, 2H); $^{13}$C NMR (CDCl$_3$) ppm 168.28, 156.09, 142.87, 136.43, 136.30, 128.98, 127.95, 127.43, 126.96, 65.81, 52.08, 45.70, 42.67, 40.14, 32.58, 28.72, 25.49, 24.65, 23.64, 21.71, 20.93; IR (KBr, cm$^{-1}$) 3316, 2938, 2860, 1718, 1634, 1526, 1452, 1416, 1340, 1246, 1162, 1092; MS m/z (MH+) calcd 502.2376, obsd 502.2363.

Anal. Calcd for C$_{26}$H$_{35}$N$_3$O$_5$S: C, 62.25; H, 7.03; N, 8.38. Found: C, 62.22; H, 6.92; N, 8.32.

EXAMPLE 16

Preparation of 1-[6-Amino-2-[[(4-methylphenyl)sulfonyl]amino]-1-oxohexyl]piperidine hydrochloride hydrate (4k)

A solution of phenylmethyl [6-[1-piperidinyl]-5-[[(4-methylphenyl)sulfonyl]amino]-6-oxohexyl]carbamate (19.20 g, 38.27 mmol) in methanol (25 mL) was added to a well-stirred, nitrogen-blanketed suspension of 10% palladium on carbon (9.1 g) in a 5% formic acid/methanol mixture (275 mL). The mixture was stirred at room temperature for about 4 hours before it was suction-filtered through Celite. The residue was taken up in dichloromethane and washed successively with saturated sodium bicarbonate solution and brine. Following drying and solvent removal, the residue was chromatographed on silica gel (elution with 10% methanol in dichloromethane) and subsequently treated with 20% methanolic hydrochloric acid. The solvent was removed in vacuo and there was isolated 9.10 g (65%) of the title compound as a white solid, m.p. 95°–100° C.; $^1$H NMR (D$_2$O) δ 7.70 (d, J=8.1 Hz, 2H), 8/44 (d, J=8.0 Hz, 2H), 4.23–4.19 (m, 1H), 3.35–3.19 (m, 3H), 3.07–2.94 (m, 3H), 2.42 (s, 3H), 1.72 –1.25 (m, 11H), 1.20–1.10 (m, 1H); $^{13}$C NMR (D$_2$O) ppm 171.67, 147.13, 136.85, 132.00, 129.13, 54.32, 48.70, 45.61, 41.27, 33.83, 28.30, 27.70, 26.84, 25.40, 23.85, 22.72; IR (KBr, cm$^{-1}$) 3432, 2940, 1632, 1472, 1446, 1336, 1164, 1092, 668; MS m/z (MH+-HCl) calcd 368.2008, obsd 368.2005.

Anal. Calcd for C$_{18}$H$_{29}$N$_3$O$_3$S*1.0HCl* 0.3H$_2$O: C, 52.82; H, 7.54; N, 10.27; H$_2$O, 1.32. Found: C, 51.64; H, 7.69; N, 9.71; H$_2$O, 1.19.

EXAMPLE 17

Preparation of
1-[6-[(3-Amino-1,2,5-thiadiazol-4-yl)amino]-2-[[[4-methylphenyl]sulfonyl]amino]-1-oxohexyl]piperidine S-oxide (6k)

Obtd 1.95 g (33%, pure), also 1.72 g (29%, slightly impure), white solid, m.p. 220°–225° C. (MeOH-/ETOAc, dec.); $^1$H NMR (CD$_3$SOCD$_3$) δ 8.26 (br m, 0.25H), 8.02–7.99 (m, 1H), 7.64–7.61 (m, 1 H), 7.60 (d, J=8.2 Hz, 2H), 7.31 (d, J=8.2 Hz, 2H), 4.11–4.02 (m, 2H), 3.16 (m, 4H), 3.14 (d, J=5.2 Hz, 1H), 3.04–2.98 (m, 1H), 2.32 (s, 3H), 1.46–1.26 (2m, 12H), 1.06 (br s, 1H); $^{13}$C NMR (CD$_3$SOCD$_3$) ppm 168.30, 157.77, 157.51, 142.63, 137.93, 129.33, 126.84, 48.69, 45.82, 43.24, 42.39, 32.05, 27.39, 25.90, 24.97, 23.89, 22.32, 21.00; IR (KBr, cm$^{-1}$) 3346, 3266, 3068, 2938, 2860 1616, 1582, 1444, 1326, 1162, 1092, 1060, 814, 666; MS m/z (MH+) calcd 483.1842, obsd 483.1835.

Anal. Calcd for C$_{20}$H$_{30}$N$_6$O$_4$S$_2$°0.1H$_2$O: C, 49.59; H, 6.29; N, 17.35; H$_2$O, 0.37. Found: C, 48.30; H, 6.15; N, 16.84; H$_2$O, 0.55.

EXAMPLE 18

Preparation of
1-[6-[(2-amino-1,2-diiminoethyl)aminol]-2-[[(4-methylphenyl)sulfonyl]amino]-1-oxohexyl]piperidine dihydrochloride (7k)

Concentrated hydrochloric acid (0.70 mL) was added to a suspension of 1-[6-(3-amino-1,2,5-thiadiazol-4-yl)-2-[[(4-methylphenyl)sulfonyl]amino]-1-oxohexyl]piperidine S-oxide (0.50 g, 1.04 mmol) in methanol (10 mL). The mixture was stirred at room temperature for about 5 hours before it was concentrated down to dryness with ethanol (5 mL) added intermittently in order to drive off the excess hydrochloric acid. There was isolated 0.60 g (100%) of the title compound as a dense, white solid, m.p. 102°–150° C. (dec. at 153° C., closed tube); $^1$H NMR (D$_2$O) δ 7.69 (d, J=8.3 Hz, 2H), 7.43 (d, J=8.3 Hz, 2H), 4.23–4.19 (m, 1H), 3.46–3.39 (m, 2H), 3.29–3.15 (2m, 2H), 3.06–2.98 (m, 1H), 2.41 (s, 3H), 1.76–1.69 (m, 2H), 1.61–1.25 (m, 8H), 1.18–1.05 (m, 1H); $^{13}$C NMR (D$_2$O) ppm 171.69, 158.03, 155.39, 147.27, 136.52, 132.01, 130.50, 129.08, 54.26, 48.73, 45.63, 45.39, 33.74, 27.75, 27.68, 26.82, 25.34, 24.08, 22.64; IR (KBr, cm$^{-1}$) 3412–2942, 1692, 1626, 1446, 1162, 1092, 668, 560; MS m/z (MH+-2HCl) calcd for C$_{20}$H$_{32}$N$_6$O$_3$S-2HCl 437.2335, obsd 437.2325.

We claim:

1. Compounds having the Formula

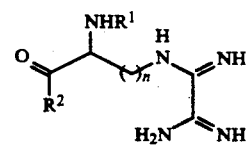

wherein
R$_1$ is dimethylaminonaphthalenesulfonyl, p-toluene sulfonyl or 2-naphthylene sulfonylglycine;
R$^2$ is piperidino, substituted piperidino, wherein the substituents are C$_1$–C$_5$ alkyl, morpholino, and hompiperidino; and
n is 1–5;
and their salts and hydrate; hereof.

2. The compound of claim 1 which is 1-[5-[(2-amino-1,2-diiminoethyl)amino]-2-[[[5-(dimethylamino)-1-naphthalenyl]sulfonyl]amino]-1-oxopentyl]-4-ethylpiperidine.

3. The compound of claim 1 which is 1-[5-[(2-amino-1,2-diiminoethyl)amino]-2-[[[5-(dimethylamino)-1-naphthalenyl]sulfonyl]amino]-1-oxopentyl]-4-methylpiperidine.

4. The compound of claim 1 which is 1-[5-[(2-amino-1,2-diiminoethyl)amino]-2-[[[5-(dimethylamino)-1-naphthalenyl]sulfonyl]amino]-1-oxopentyl]piperidine.

5. The compound of claim 1 which is 1-[5-[(2-amino-1,2-diiminoethyl)amino]-2-[[[5-(dimethylamino)-1-naphthalenyl]sulfonyl]amino]-1-oxopentyl]morpholine.

6. The compound of claim 1 which is 1-[5-[(2-amino-1,2-diiminoethyl)amino]-2-[[[5-(dimethylamino)-1-naphthalenyl]sulfonyl]amino]-1-oxopentyl]homopiperidine.

7. The compound of claim 1 which is 1-[5-[2-(amino-1,2-diiminoethyl)amino]-2-[[(4-methylphenyl)sulfonyl]amino]-1-oxopentyl]-4-methylpiperidine.

8. The compound of claim 1 which is 1-[6-[(2-amino-1,2diiminoethyl)amino]-2-[[(4-methylphenyl)sulfonyl]amino]-1-oxohexyl]piperidine.

9. The compound of claim 1 which is 1-[3-[(2-amino-1,2-diiminoethyl)amino]-2-[[(4-methylphenyl)sulfonyl]amino]-1-oxopropyl]piperidine.

10. The compound of claim 1 which is 1-[4-[(2-amino-1,2-diiminoethyl)amino]-2-[[(4-methylphenyl)sulfonyl]amino]-1-oxobutyl]piperidine.

11. The compound of claim 1 which is N-[3-[(2-amino-1,2-diiminoethyl)amino]-1-[[(1-piperidinyl)carbonyl]propyl]-2-[[(2-napthalenyl)sulfonyl]amino]]acetamide.

12. The compound of claim 1 which is 1-[4-[(2-amino-1,2-diiminoethyl)amino]-2-[[[5-(dimethylamino)-1-naphthalenyl]sulfonyl]amino]-oxobutyl]-4-methylpiperidine.

13. The compound of claim 1 which is N-[4-[(2-amino-1,2-diiminoethyl)amino]-1-[[(1-piperidinyl)carbonyl]butyl]-2-[[(2-naphthalenyl)sulfonyl]amino]]acetamide.

14. A pharmaceutical composition which comprises at least one compound of claim 1 and one or more pharmaceutically acceptable carrier or diluent.

15. A method of treating thrombosis, ischemia or stroke in a mammalian host in need thereof which comprises administering to said host an effective amount of a compound of claim 1.

* * * * *